United States Patent
Ahmed et al.

(10) Patent No.: US 8,673,969 B2
(45) Date of Patent: Mar. 18, 2014

(54) SUBSTITUTED 4-β-ACRYLAMIDOPODOPHYLLOTOXIN CONGENERS AS ANTITUMOUR ANTIBIOTICS AND THE PROCESS FOR PREPARATION THEREOF

(75) Inventors: Kamal Ahmed, Hyderabad (IN); Suresh Paidakula, Hyderabad (IN); Ashwini Kumar Banala, Hyderabad (IN); Adla Malla Reddy, Hyderabad (IN); Papagiri Venkat Reddy, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/883,938

(22) PCT Filed: Mar. 9, 2011

(86) PCT No.: PCT/IN2011/000157
§ 371 (c)(1),
(2), (4) Date: May 7, 2013

(87) PCT Pub. No.: WO2012/063250
PCT Pub. Date: May 18, 2012

(65) Prior Publication Data
US 2013/0225672 A1    Aug. 29, 2013

(30) Foreign Application Priority Data
Nov. 11, 2010    (IN) ............................ 2697/DEL/2010

(51) Int. Cl.
*A61K 31/335*    (2006.01)
*C07D 493/04*    (2006.01)

(52) U.S. Cl.
USPC ............................................ 514/463; 549/298

(58) Field of Classification Search
USPC ............................................ 514/463; 549/298
See application file for complete search history.

(56) References Cited

U.S. PATENT DOCUMENTS

| | | | |
|---|---|---|---|
| 2004/0192621 A1* | 9/2004 | Nihei et al. | 514/27 |
| 2007/0066837 A1* | 3/2007 | Kamal et al. | 549/298 |
| 2008/0275248 A1* | 11/2008 | Ahmed et al. | 548/159 |
| 2009/0170843 A1* | 7/2009 | Imbert et al. | 514/232.8 |

* cited by examiner

*Primary Examiner* — Raymond Henley, III
(74) *Attorney, Agent, or Firm* — Abelman, Frayne & Schawb (57) ABSTRACT

The present invention provides compounds of general formula (3) as useful potential antitumour agents against human cancer cell lines. The present invention further provides a process for the synthesis of 4β-acrylamidopodophyllotoxin congeners of general formula (3), wherein R and R1 are an aryl group and R is selected from 3,4,5-trimethoxyphenyl or 2-methoxy phenyl and R1 is selected from the group consisting of 4-hydroxy-3-methoxyphenyl, 3-hydroxy-4-methoxyphenyl, 4-fluoro-3-methoxyphenyl, 3-fluoro-4-methoxyphenyl, 2-fluoro-5-methoxyphenyl, 2-fluoro-4-methoxyphenyl, 4-hydroxy-3-nitrophenyl, 4-methoxy-3-nitrophenyl, 4-nitrophenyl, 3-nitrophenyl, 2-nitro phenyl, 4-methoxyphenyl, 3-methoxyphenyl and 4-hydroxyphenyl.

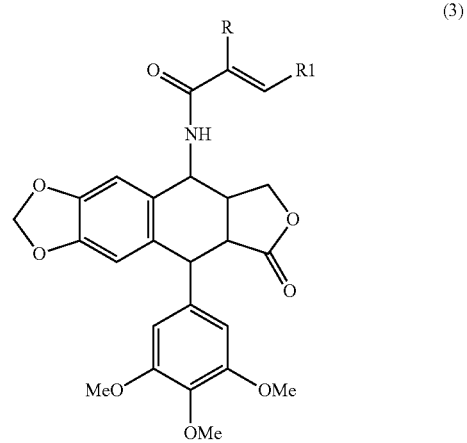

18 Claims, 1 Drawing Sheet

Scheme 1

SUBSTITUTED 4-β-ACRYLAMIDOPODOPHYLLOTOXIN CONGENERS AS ANTITUMOUR ANTIBIOTICS AND THE PROCESS FOR PREPARATION THEREOF

RELATED APPLICATIONS

This application is a §371 of PCT/IN2011/000157 filed Mar. 9, 2011, and claims priority from Indian Patent Application No. 2697/DEL/2010 filed Nov. 11, 2010, both incorporated by reference in their entirety.

FIELD OF THE INVENTION

The present invention relates to substituted 4β-acrylamidopodophyllotoxin congeners of general formula 3 as antitumour antibiotics.

Present invention further relates to a process for the synthesis of 4β-acrylamidopodophyllotoxin congeners of general formula 3, General formula 3 wherein R and R1 are an aryl group and R is selected from 3,4,5-trimethoxyphenyl or 2-methoxy phenyl and R1 is selected from the group consisting of 4-hydroxy-3-methoxyphenyl, 3-hydroxy-4-methoxyphenyl, 4-fluoro-3-methoxyphenyl, 3-fluoro-4-methoxyphenyl, 2-fluoro-5-methoxyphenyl, 2-fluoro-4-methoxyphenyl, 4-hydroxy-3-nitrophenyl, 4-methoxy-3-nitrophenyl, 4-nitrophenyl, 3-nitrophenyl, 2-nitro phenyl, 4-methoxyphenyl, 3-methoxyphenyl and 4-hydroxyphenyl.

BACKGROUND OF THE INVENTION

Figure 1:
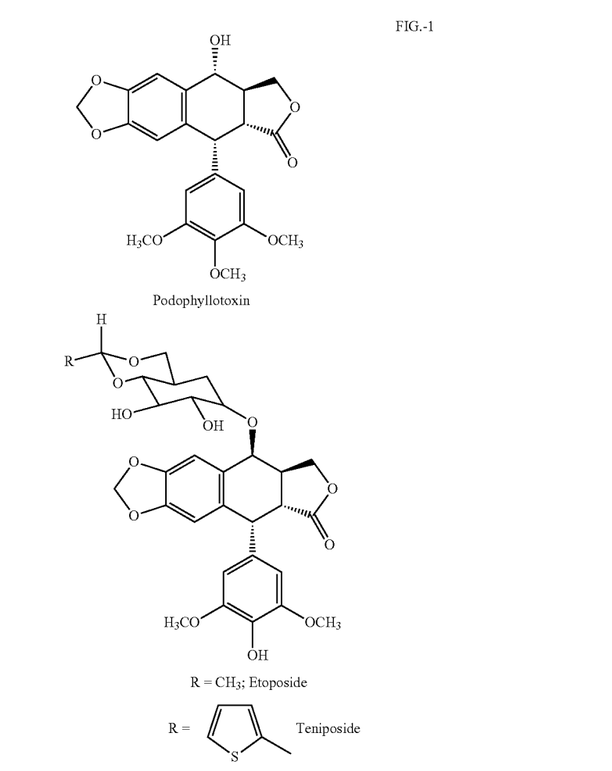

Etoposide and teniposide are semisynthetic podophyllotoxin derivatives that are in clinical usage as anticancer drugs FIG. 1 (Chen. Y. Z.; Wang. Y. G.; Tian, X.; Li, J. X. *Curr. Sci* 1990, 59, 517; Wang, J. Z.; Tian, X.; Tsumura, H.; Shimura, K.; Ito, H. *Anti-cancer Drug Design*, 1993, 8, 193). It is believed that analogues of 4'-demethyl epipodophyllotoxin exert their antitumour activity through stabilization of a cleavable complex between DNA and type-II DNA topoisomerase, this leads ultimately to inhibition of DNA catenation activity and produces single and double strand breaks (Satio, H.; Yoshikawa, H.; Nishimura, Y.; Kondo, S.; Takeuchi, T.; Umezawa, H. *Chem Pharm. Bull.* 1986, 34, 3733; Chen, Y. Z.; Wang, Y. G.; Li, J. X.; Tian, X.; Jia. Z. P.; Zhang, Z. Y. *Life Sci.* 1989, 45, 2569). A number of studies have been carried out on the structural modification of glycoside by amino substituents that has improved the inhibitory activity on human DNA topoisomerase-II as well as stronger activity in causing cellular protein length DNA breakage (Lee, K. H.; Imakura, Y.; Haruna, M.; Beers, S. A.; Thurston, L. S.; Dai, H. J.; Chen, C. H.; Liu, S. Y.; Cheng, Y. C. *J. Nat. Prod.* 1989, 52, 606; Liu, S. Y; Hawang, B. D.; Haruna, M.; Imakura, Y.; Lee, K. H.; Cheng, Y. C. *Mol. Pharmcol.* 1989, 36, 8; Lee, K, H.; Beers, S. A.; Mori, M.; Wang, Z. Q.; Kuo, Y. H.; Li, L.; Liu, S. Y.; Cheng, Y. C.; *J. Med. Chem.* 1990, 33, 1364. Etoposide values are taken from NCI data base those reference, Kamal, A.; Gayatri, N. L.; Reddy, D. R.; Reddy, P. S. M. M.; Arifuddin, M.; Dastidar, S. G.; Kondapi, M. A.; Rajkumar M. *Bioorg. Med. Chem.* 2005, 13, 6218; Kamal, A.; Kumar, B. A.; Arifuddin, M.; Dastidar, S. G. *Bioorg. Med. Chem.* 2003, 11, 5135). In this context a large number of $4_{Lx}$-acrylamido derivatives of podophyllotoxin based compounds have been synthesized and investigated for their antitumour activity.

FIG.-1

OBJECTIVE OF THE INVENTION

The main objective of the invention is to provide substituted 4β-acrylamidopodophyllotoxin congeners as useful antitumour antibiotics.

Another object of the present invention is to provide a process for the synthesis of 4β-acrylamido derivatives of podophyllotoxin as useful anticancer agents.

Another object of the present invention is to provide compounds based on the podophyllotoxin in good yields.

SUMMARY OF THE INVENTION

Accordingly, present invention provides substituted 4β-acrylamidopodophyllotoxin congener compounds of general formula 3

General formula 3 wherein R and R1 are an aryl group and R is selected from 3,4,5-trimethoxyphenyl or 2-methoxy phenyl and R1 is selected from the group consisting of 4-hydroxy-3-methoxyphenyl, 3-hydroxy-4-methoxyphenyl, 4-fluoro-3-methoxyphenyl, 3-fluoro-4-methoxyphenyl, 2-fluoro-5-methoxyphenyl, 2-fluoro-4-methoxyphenyl, 4-hydroxy-3-nitrophenyl, 4-methoxy-3-nitrophenyl, 4-nitrophenyl, 3-nitrophenyl, 2-nitro phenyl, 4-methoxyphenyl, 3-methoxyphenyl and 4-hydroxyphenyl.

In an embodiment of the present invention, chemical formula of the representative compounds are:
4β-(E)-3-(4-hydroxy-3-methoxyphenyl)-2-(3,4,5-trimethoxyphenyl)acrylamidopodophyllotoxin (3a);
4β-(E)-3-(3-hydroxy-4-methoxyphenyl)-2-(3,4,5-trimethoxyphenyl)acrylamidopodophyllotoxin (3b);
4β-(E)-3-(4-fluoro-3-methoxyphenyl)-2-(3,4,5-trimethoxyphenyl)acrylamidopodophyllotoxin (3c);
4β-(E)-3-(3-fluoro-4-methoxyphenyl)-2-(3,4,5-trimethoxyphenyl)acrylamidopodophyllotoxin (3d);
4β-(E)-3-(2-fluoro-5-methoxyphenyl)-2-(3,4,5-trimethoxyphenyl)acrylamidopodophyllotoxin (3e);
4β-(E)-3-(2-fluoro-4-methoxyphenyl)-2-(3,4,5-trimethoxyphenyl)acrylamidopodophyllotoxin (3f);
4β-(E)-3-(4-hydroxy-3-nitrophenyl)-2-(3,4,5-trimethoxyphenyl)acrylamidopodophyllotoxin (3g);
4β-(E)-3-(4-methoxy-3-nitrophenyl)-2-(3,4,5-trimethoxyphenyl)acrylamidopodophyllotoxin (3h);
4β-(E)-3-(4-nitrophenyl)-2-(3,4,5-trimethoxyphenyl)acrylamidopodophyllotoxin (3i);
4β-(E)-3-(3-nitrophenyl)-2-(3,4,5-trimethoxyphenyl)acrylamidopodophyllotoxin (3j);
4β-(E)-3-(2-nitrophenyl)-2-(3,4,5-trimethoxyphenyl)acrylamidopodophyllotoxin (3k);
4β-(E)-2-(2-methoxyphenyl)-3-(4-nitrophenyl)acrylamidopodophyllotoxin (3l);
4β-(E)-2-(2-methoxyphenyl)-3-(2-nitrophenyl)acrylamidopodophyllotoxin (3m);
4β-(E)-3-(4-methoxyphenyl)-2-(3,4,5-trimethoxyphenyl)acrylamidopodophyllotoxin (3n);
4β-(E)-3-(3-methoxyphenyl)-2-(3,4,5-trimethoxyphenyl)acrylamidopodophyllotoxin (3o);
4β-(E)-3-(4-hydroxyphenyl)-2-(3,4,5-trimethoxyphenyl)acrylamidopodophyllotoxin (3p);

In an another embodiment of the present invention, the structural formula of the representative compounds 3a-p are:

3a

3b

3i

3l

3j

3m

3k

3n

-continued

3o

3p

In yet another embodiment of the present invention, the said compounds are useful as antitumour antibiotics.

Yet another embodiment of the present invention provides a process for the preparation of 4β-acrylamidopodophyllotoxin congeners of general formula 3 and the said process comprising the steps of:
i. dissolving 4β-acrylamidopodophyllotoxin of formula 1 in a solvent to obtain a solution;

1 ii. adding aromatic acrylic acid of formula 2a-p wherein R and R1 are an aryl group and R is selected from 3,4,5-trimethoxyphenyl or 2-methoxy phenyl and R1 is selected from the group consisting of 4-hydroxy-3-methoxyphenyl, 3-hydroxy-4-methoxyphenyl, 4-fluoro-3-methoxyphenyl, 3-fluoro-4-methoxyphenyl, 2-fluoro-5-methoxyphenyl, 2-fluoro-4-methoxyphenyl, 4-hydroxy-3-nitrophenyl, 4-methoxy-3-nitrophenyl, 4-nitrophenyl, 3-nitrophenyl, 2-nitro phenyl, 4-methoxyphenyl or 3-methoxyphenylin in the solution as obtained in step (i) with coupling reagents and acetic acid followed by stirring at temperature in the range of 25 to 30° C. for a period in the range of 2 to 3 h;

2a-p iii. filtering, washing with saturated solution of NaHCO$_3$, 10% hydrochloric acid and followed by water;
iv. drying the washed filterate as obtained in step (iii) over anhydrous Na$_2$SO$_4$ followed by chromatography through silica gel using an eluent to obtain the pure product.

In yet another embodiment of the present invention, the solvent used is selected from the group consisting of dichloromethane, chloroform and tetrahydrofuran, preferably dichloromethane.

In yet another embodiment of the present invention, the coupling reagents used are EDCI and HOBt both.

In yet another embodiment of the present invention, the eluent used is ethyl acetate/hexane in the ratio ranging between 1:1 to 1:4.

In yet another embodiment of the present invention, said compounds shows in-vitro anticancer activity against human tumour cells derived from five cancer types selected from the group consisting of breast cancer cell line (MCF-7, Zr-75-1), oral cancer cell line (KB, Gurav, DWD), colon cancer cell line (Colo 205), lung cancer cell line (A549, Hop 62) and ovarion cancer cell line (A-2780).

In yet another embodiment of the present invention, concentration of the Substituted 4β-acrylamidopodophyllotoxin congeners of general formula 3 used for in vitro activity against breast cancer cell lines (Zr-75-1) for GI$_{50}$ is in the range of 0.18-2.7 μM at an exposure period of at least 48 hrs.

In yet another embodiment of the present invention, concentration of the Substituted 4β-acrylamidopodophyllotoxin congeners of general formula 3 used for in vitro activity against breast cancer cell lines (MCF-7) for GI$_{50}$ is in the range of 2.4-2.9 μM at an exposure period of at least 48 hrs.

In yet another embodiment of the present invention, concentration of the Substituted 4β-acrylamidopodophyllotoxin congeners of general formula 3 used for in vitro activity against oral cancer cell lines (KB) for GI$_{50}$ is in the range of 2.1-2.7 μM at an exposure period of at least 48 hrs.

In yet another embodiment of the present invention, concentration of the Substituted 4β-acrylamidopodophyllotoxin congeners of general formula 3 used for in vitro activity against oral cancer cell lines (Gurav) for GI$_{50}$ is in the range of 0.18-2.7 μM at an exposure period of at least 48 hrs.

In yet another embodiment of the present invention, concentration of the Substituted 4β-acrylamidopodophyllotoxin congeners of general formula 3 used for in vitro activity against oral cancer cell lines (DWD) for $GI_{50}$ is in the range of <0.1-2.9 μM at an exposure period of at least 48 hrs.

In yet another embodiment of the present invention, concentration of the Substituted 4β-acrylamidopodophyllotoxin congeners of general formula 3 used for in vitro activity against colon cancer cell lines (Colo205) for $GI_{50}$ is in the range of 0.17-2.7 μM at an exposure period of at least 48 hrs.

In yet another embodiment of the present invention, concentration of the Substituted 4β-acrylamidopodophyllotoxin congeners of general formula 3 used for in vitro activity against lung cancer cell lines (A-549) for $GI_{50}$ is in the range of <0.1-2.9 μM at an exposure period of at least 48 hrs.

In yet another embodiment of the present invention, concentration of the Substituted 4β-acrylamidopodophyllotoxin congeners of general formula 3 used for in vitro activity against lung cancer cell lines (Hop62) for $GI_{50}$ is in the range of 0.17-2.9 μM at an exposure period of at least 48 hrs.

In yet another embodiment of the present invention, concentration of the Substituted 4β-acrylamidopodophyllotoxin congeners of general formula 3 used for in vitro activity against ovarian cancer cell lines (A-2780) for $GI_{50}$ is in the range of <0.1-2.7 μM at an exposure period of at least 48 hrs.

BRIEF DESCRIPTION OF THE DRAWINGS

Scheme 1 discloses the process for the synthesis of new podophyllotoxin analogues as anticancer agents producing the novel derivatives of the podophyllotoxin in good yields. 4β-acrylamidopodophyllotoxin of formula 1 reacts with aromatic acrylic acid of formula 2(a) to 2(e) to yield substituted 4β-acrylamidopodophyllotoxin congener compounds of formula 3(a) to 3(e) respectively.

DETAILED DESCRIPTION OF THE INVENTION

The process of the present invention for the synthesis of C-4β-N-linked derivatives of podophyllotoxin as anticancer agents produces the novel derivatives of the podophyllotoxin in good yields; where in the key step for the synthesis of these analogues is by C-4β-amino podophyllotoxin, which has been coupled with different types of aromatic acrylic acids to afford the 4β-acrylamido derivatives of podophyllotoxin.

Thus the present invention provides new class of podophyllotoxin analogues, which were synthesized.

In these efforts new 4β-acrylamido derivatives of podophyllotoxin have been synthesized and evaluated for their cytotoxicity and anticancer potency compared to adiramycin. The synthesis of these compounds has been carried out as described in the Scheme 1 using podophyllotoxin. These new analogues of podophyllotoxin congeners coupled at C-4 position have shown promising anticancer activity in selected human cancer cell lines. This resulted in design and synthesis of new congeners as illustrated in Scheme 1.

EXAMPLES

The following examples are given by way of illustration and therefore should not be construed to limit the scope of the present invention.

Example 1

4β-(E)-3-(4-hydroxy-3-methoxyphenyl)-2-(3,4,5-trimethoxyphenyl)acrylamidopodophyllotoxin (3a)

4β-aminopodophyllotoxin (formula 1) (200 mg, 0.48 mmol) was dissolved in 20 ml of dried dichloromethane, followed by addition of aromatic acrylic acid 2a (220 mg, 0.57 mmol) and EDCI (N-(3-Dimethylaminopropyl)-N'-ethyl-carbodiimide hydrochloride) (108 mg, 0.57 mmol) and catalytic amount of HOBt (1-HydroxylBenztriazole). The reaction mixture was stirred at 27° C. for 3 h. Acetic acid (0.4 ml) was added. The reaction mixture was filtered. The filtrate was washed with saturated solution of $NaHCO_3$, 10% hydrochloric acid and water respectively, dried over anhydrous $Na_2SO_4$ and chromatographed through silica gel using ethyl acetate/hexane (4:6) as an eluent to obtain the pure product. Yield 95%. Mp: 134-137° C., $[\alpha]_D^{25}=-12.9$ (c=0.5 in $CHCl_3$); $^1H$ NMR (400 MHz, $CDCl_3$) δ: 2.55-2.63 (dd, 1H, J=4.5, 4.5 Hz), 2.86-3.00 (m, 1H), 3.53 (s, 3H), 3.73 (s, 6H), 3.75 (s, 9H), 3.81 (s, 3H), 4.23-4.31 (m, 1H), 4.39-4.48 (m, 2H), 5.30 (t, 1H), 5.72 (d, 1H, J=6.7 Hz), 5.95 (d, 2H, J=3.0 Hz), 6.14-6.24 (m, 3H), 6.34-6.47 (m, 4H), 6.70-6.77 (m, 3H), 7.68 (s, 1H); $^{13}C$ NMR (75 MHz, $CDCl_3$) δ: 36.8, 40.4, 43.1, 47.8, 54.6, 55.6, 55.8, 59.8, 60.0, 68.6, 101.1, 102.8, 107.2, 108.0, 109.1, 109.2, 109.4, 112.6, 115.0, 121.1, 124.7, 126.0, 130.1, 131.4, 131.6, 132.1, 132.4, 133.3, 135.2, 135.7, 136.2, 137.0, 146.5, 146.7, 147.1, 147.3, 151.9, 153.2, 167.6, 174.5; MS (ESI): 756 [$M^++H$].

Example 2

4β-(E)-3-(3-hydroxy-4-methoxyphenyl)-2-(3,4,5-trimethoxyphenyl)acrylamido podophyllotoxin (3b)

4β-aminopodophyllotoxin (formula 1) (200 mg, 0.48 mmol) was dissolved in 20 ml of dried dichloromethane, followed by addition of aromatic acrylic acid 2b (220 mg, 0.57 mmol) and EDCI (108 mg, 0.57 mmol) and catalytic amount of HOBt. The reaction mixture was stirred at 28° C. for 3 h. Acetic acid (0.4 ml) was added. The reaction mixture was filtered. The filtrate was washed with saturated solution of $NaHCO_3$, 10% hydrochloric acid and water respectively, dried, over anhydrous $Na_2SO_4$ and chromatographed through silica gel using ethyl acetate/hexane (4:6) as an eluent to obtain the pure product. Yield 97%. Mp: 145-147° C., $[\alpha]_D^{25}=-6.9$ (c=0.5 in $CHCl_3$); $^1H$ NMR (400 MHz, $CDCl_3$) δ: 2.52-2.63 (dd, 1H, J=4.6, 4.6 Hz), 2.85-3.02 (m, 1H), 3.75 (s, 9H), 3.78 (s, 3H), 389 (s, 6H), 4.24-4.33 (dd, 1H, J=4.6, 4.6 Hz), 4.43-4.52 (dd, 2H, J=6.2, 6.2 Hz), 5.31 (t, 1H), 5.67 (d, 1H, J=7.8 Hz), 5.97 (d, 2H, J=4.6 Hz), 6.24 (s, 2H), 6.42 (s, 2H), 6.47 (s, 1H), 6.52-6.70 (m, 3H), 6.75 (s, 1H), 7.68 (s, 1H); $^{13}C$ NMR (75 MHz, $CDCl_3$) δ: 36.7, 40.4, 43.1, 47.7, 55.3, 55.6, 55.7, 59.8, 60.0, 68.6, 101.1, 107.1, 108.0, 109.1, 109.2, 111.3, 116.6, 121.9, 127.5, 130.2, 131.1, 132.0, 133.5, 134.5, 135.7, 136.2, 137.1, 145.7, 146.5, m 147.1, 148.0, 151.9, 152.9, 168.0, 174.5; MS (ESI): 778 [$M^++Na$].

Example 3

4β-(E)-3-(4-fluoro-3-methoxyphenyl)-2-(3,4,5-trimethoxyphenyl)acrylamidopodophyllotoxin (3c)

4β-aminopodophyllotoxin (formula 1) (200 mg, 0.48 mmol) was dissolved in 20 ml of dried dichloromethane, followed by addition of aromatic acrylic acid 2c (205 mg, 0.57 mmol) and EDCI (108 mg, 0.57 mmol) and catalytic amount of HOBt. The reaction mixture was stirred at 27° C. for 3 h. Acetic acid (0.4 ml) was added. The reaction mixture was filtered. The filtrate was washed with saturated solution of $NaHCO_3$, 10% hydrochloric acid and water respectively, dried over anhydrous $Na_2SO_4$ and chromatographed through silica gel using ethyl acetate/hexane (3:7) as an eluent to obtain the pure product. Yield 98%. Mp: 144-146° C.,

[α]$_D^{25}$=−1.7 (c=0.5 in CHCl$_3$); $^1$H NMR (400 MHz, CDCl$_3$) δ: 2.52-2.63 (dd, 1H, J=5.1, 5.1 Hz), 2.85-3.01 (m, 1H), 3.53 (s, 3H), 3.74 (s, 6H), 375 (s, 6H), 3.77 (s, 3H), 3.82 (s, 3H), 3.88 (t, 1H), 4.41-4.50 (dd, 2H, J=6.6, 5.8 Hz), 5.23-5.30 (m, 1H), 5.73 (d, 1H, J=6.6 Hz), 5.95 (d, 2H, J=3.6 Hz), 6.22 (s, 2H), 6.43 (s, 2H), 6.44 (s, 1H), 6.48-6.54 (dd, 1H, J=1.4, 1.4 Hz), 6.72-6.76 (m, 2H), 6.87-6.98 (dd, 1H, J=8.0, 8.0 Hz), 7.70 (s, 1H); $^{13}$C NMR (75 MHz, CDCl$_3$) δ: 36.7, 40.3, 43.1, 47.8, 55.1, 55.6, 55.7, 59.7, 59.8, 68.5, 101.1, 107.0, 108.0, 109.1, 109.2, 114.3, 115.4, 115.6, 123.1, 123.2, 130.0, 130.8, 131.8, 132.1, 133.5, 135.7, 135.8, 136.2, 137.2, 146.5, 147.1, 149.4, 151.9, 153.1, 167.4, 174.5; MS (ESI): 758 [M$^+$+H].

Example 4

4β-(E)-3-(3-fluoro-4-methoxyphenyl)-2-(3,4,5-trimethoxyphenyl)acrylamidopodophyllotoxin (3d)

4β-aminopodophyllotoxin (formula 1) (200 mg, 0.48 mmol) was dissolved in 20 ml of dried dichloromethane, followed by addition of aromatic acrylic acid 2d (205 mg, 0.57 mmol) and EDCI (108 mg, 0.57 mmol) and catalytic amount of HOBt. The reaction mixture was stirred at 29° C. for 3 h. Acetic acid (0.4 ml) was added. The reaction mixture was filtered. The filtrate was washed with saturated solution of NaHCO$_3$, 10% hydrochloric acid and water respectively, dried over anhydrous Na$_2$SO$_4$ and chromatographed through silica gel using ethyl acetate/hexane (3:7) as an eluent to obtain the pure product. Yield 94%. Mp: 159-160° C., [α]$_D^{25}$=+13.9 (c=0.5 in CHCl$_3$); $^1$H NMR (400 MHz, CDCl$_3$) δ: 2.54-2.63 (dd, 1H, J=5.2, 5.2 Hz), 2.87-2.97 (m, 1H), 3.38 (t, 1H), 3.74 (s, 6H), 3.75 (s, 6H), 3.77 (s, 3H), 3.86 (s, 3H), 3.87 (s, 3H), 4.41-4.49 (m, 2H), 5.26 (t, 1H), 5.74 (d, 1H, J=6.7 Hz), 5.95 (d, 2H, J=6.0 Hz), 6.22 (s, 2H), 6.40 (s, 2H), 6.44 (s, 1H), 6.62 (d, 1H, J=12.8 Hz), 6.73 (s, 1H), 6.76-6.87 (m, 2H), 7.66 (s, 1H); $^{13}$C NMR (75 MHz, CDCl$_3$)—: 36.7, 40.4, 43.1, 47.7, 55.6, 55.7, 59.7, 60.0, 68.5, 101.1, 106.9, 108.0, 109.1, 109.2, 113.2, 116.2, 116.5, 126.9, 127.8, 130.0, 130.7, 132.0, 133.1, 134.9, 135.7, 136.2, 137.3, 146.5, 147.1, 151.9, 152.2, 153.1, 167.5, 174.5; MS (ESI): 758 [M$^+$+H].

Example 5

4β-(E)-3-(2-fluoro-5-methoxyphenyl)-2-(3,4,5-trimethoxyphenyl)acrylamidopodophyllotoxin (3e)

4β-aminopodophyllotoxin (formula 1) (200 mg, 0.48 mmol) was dissolved in 20 ml of dried dichloromethane, followed by addition of aromatic acrylic acid 2e (205 mg, 0.57 mmol) and EDCI (108 mg, 0.57 mmol) and catalytic amount of HOBt. The reaction mixture was stirred at 27° C. for 3 h. Acetic acid (0.4 ml) was added. The reaction mixture was filtered. The filtrate was washed with saturated solution of NaHCO$_3$, 10% hydrochloric acid and water respectively, dried over anhydrous Na$_2$SO$_4$ and chromatographed through silica gel using ethyl acetate/hexane (3:7) as an eluent to obtain the pure product. Yield 98%. Mp: 123-126° C., [−]$_D^{25}$=−12.0 (c=0.5 in CHCl$_3$); $^1$H NMR (400 MHz, CDCl$_3$) δ: 2.68-2.75 (dd, 1H, J=5.2, 5.2 Hz), 2.95-3.08 (m, 1H), 3.40 (s, 3H), 3.74 (s, 6H), 375 (s, 6H), 3.80 (s, 3H), 3.84 (s, 3H), 3.90 (t, 1H), 4.49-4.55 (dd, 2H, J=60, 6.0 Hz), 5.32-5.37 (dd, 1H, J=4.5, 4.5 Hz), 5.96 (d, 2H, J=9.0 Hz), 5.99 (d, 1H, J=7.5 Hz), 6.20-6.25 (m, 1H), 6.28 (s, 2H), 6.45 (s, 2H), 6.48 (s, 1H), 6.72-6.77 (m, 1H), 6.78 (s, 1H), 6.93 (t, 1H), 7.94 (s, 1H); MS (ESI): 758 [M$^+$+H].

Example 6

4β-(E)-3-(2-fluoro-4-methoxyphenyl)-2-(3,4,5-trimethoxyphenyl)acrylamidopodophyllotoxin (3f)

4β-aminopodophyllotoxin (formula 1) (200 mg, 0.48 mmol) was dissolved in 20 ml of dried dichloromethane, followed by addition of aromatic acrylic acid 2f (205 mg, 0.57 mmol) and EDCI (108 mg, 0.57 mmol) and catalytic amount of HOBt. The reaction mixture was stirred at 30° C. for 3 h. Acetic acid (0.4 ml) was added. The reaction mixture was filtered. The filtrate was washed with saturated solution of NaHCO$_3$, 10% hydrochloric acid and water respectively, dried over anhydrous Na$_2$SO$_4$ and chromatographed through silica gel using ethyl acetate/hexane (3:7) as an eluent to obtain the pure product. Yield 96%. Mp: 123-125° C., [α]$_D^{25}$=+4.9 (c=0.5 in CHCl$_3$); $^1$H NMR (400 MHz, CDCl$_3$) δ: 2.61-2.66 (dd, 1H, J=4.7, 4.7 Hz), 2.94-3.03 (m, 1H), 3.73 (s, 6H), 3.75 (s, 6H), 3.77 (s, 3H), 3.81 (s, 3H), 3.89 (s, 3H), 3.90-3.92 (m, 1H), 4.49-4.55 (m, 2H), 5.30-5.34 (m, 1H), 5.73 (d, 1H, J=6.2 Hz), 5.96 (d, 2H, J=11.7 Hz), 6.27 (s, 2H), 6.37-6.41 (m, 1H), 6.42 (s, 2H), 6.49 (s, 1H), 6.56-6.61 (m, 2H), 6.74 (s, 1H), 7.96 (s, 1H); $^{13}$C NMR (75 MHz, CDCl$_3$) δ: 36.7, 40.2, 40.3, 43.1, 47.8, 55.9, 59.8, 59.9, 68.6, 101.0, 101.2, 101.4, 106.6, 107.0, 108.0, 109.3, 110.3, 114.8, 115.0, 125.9, 130.1, 130.4, 130.7, 132.1, 135.7, 136.2, 137.2, 146.5, 147.1, 151.9, 152.9, 160.8, 162.8, 167.6, 174.5; MS (ESI): 758 [M$^+$+H].

Example 7

4β-(E)-3-(4-hydroxy-3-nitrophenyl)-2-(3,4,5-trimethoxyphenyl)acrylamidopodophyllotoxin (3g)

4β-aminopodophyllotoxin (formula 1) (200 mg, 0.48 mmol) was dissolved in 20 ml of dried dichloromethane; followed by addition of aromatic acrylic acid 2g (214 mg, 0.57 mmol) and EDCI (108 mg, 0.57 mmol) and catalytic amount of HOBt. The reaction mixture was stirred at 27° C. for 3 h. Acetic acid (0.4 ml) was added. The reaction mixture was filtered. The filtrate was washed with saturated solution of NaHCO$_3$, 10% hydrochloric acid and water respectively, dried over anhydrous Na$_2$SO$_4$ and chromatographed through silica gel using ethyl acetate/hexane (4:6) as an eluent to obtain the pure product. Yield 98%. Mp: 184-187° C., [α]$_D^{25}$=−8.9 (c=0.5 in CHCl$_3$); $^1$H NMR (400 MHz, CDCl$_3$) δ: 2.54-2.63 (dd, 1H, J=4.5, 4.5 Hz), 2.88-3.02 (m, 1H), 3.74 (s, 6H), 3.76 (s, 6H), 3.77 (s, 3H), 3.88 (s, 3H), 4.06-4.13 (m, 1H), 4.24-4.31 (dd, 1H, J=3.7, 4.5 Hz), 4.41-4.49 (m, 2H), 5.30 (t, 1H), 5.78 (d, 1H, J=6.7 Hz), 5.96 (d, 2H, J=4.5 Hz), 6.22 (s, 2H), 6.40 (s, 2H), 6.43 (s, 1H), 6.73 (s, 1H), 7.00 (d, 1H, J=9.0 Hz), 7.28 (d, 1H, J=9.0 Hz), 7.70 (s, 1H), 7.74 (s, 1H); $^{13}$C NMR (75 MHz, CDCl$_3$) δ: 36.7, 40.4, 43.1, 47.7, 55.6, 55.8, 59.8, 60.0, 101.1, 106.9, 108.0, 109.1, 109.2, 118.7, 126.1, 126.2, 130.0, 130.4, 132.1, 135.7, 136.3, 136.4, 137.5, 146.5, 147.1, 151.9, 153.2, 167.4, 174.5; MS (ESI): 794 [M$^+$+Na].

Example 8

4β-(E)-3-(4-methoxy-3-nitrophenyl)-2-(3,4,5-trimethoxyphenyl)acrylamidopodophyllotoxin (3h)

4β-aminopodophyllotoxin (formula 1) (200 mg, 0.48 mmol) was dissolved in 20 ml of dried dichloromethane, followed by addition of aromatic acrylic acid 2h (221 mg, 0.57 mmol) and EDCI (108 mg, 0.57 mmol) and catalytic amount of HOBt. The reaction mixture was stirred at 27° C. for 3 h. Acetic acid (0.4 ml) was added. The reaction mixture was filtered. The filtrate was washed with saturated solution of NaHCO$_3$, 10% hydrochloric acid and water respectively, dried over anhydrous Na$_2$SO$_4$ and chromatographed through silica gel using ethyl acetate/hexane (3:7) as an eluent to obtain the pure product. Yield 97%. Mp: 140-143° C., $[\alpha]_D^{25}$=−23.9 (c=0.5 in CHCl$_3$); $^1$H NMR (400 MHz, CDCl$_3$) δ: 2.56-2.63 (dd, 1H, J=5.3, 5.3 Hz), 2.87-3.00 (m, 1H), 3.36 (t, 1H, J=7.0, 7.0 Hz), 3.73 (s, 6H), 3.75 (s, 6H), 3.76 (s, 3H), 3.94 (s, 3H), 3.95 (s, 3H), 4.39-4.46 (m, 2H), 5.25 (t, 1H, J=5.3, 6.2 Hz), 5.81 (d, 1H, J=6.2 Hz), 5.94 (d, 2H, J=5.3 Hz), 6.20 (s, 2H), 6.38 (s, 2H), 6.71 (s, 1H), 6.91 (d, 1H, J=7.9 Hz), 7.25 (s, 1H), 7.27 (d, 1H, J=7.9 Hz), 7.34 (s, 1H), 7.68 (s, 1H); $^{13}$C NMR (75 MHz, CDCl$_3$) δ: 36.7, 43.1, 46.5, 47.8, 48.5, 55.7, 55.8, 56.7, 59.8, 60.0, 101.2, 106.9, 108.1, 109.2, 109.3, 114.0, 125.8, 127.4, 130.0, 130.4, 131.8, 132.1, 135.7, 136.2, 136.3, 137.6, 138.6, 146.5, 147.1, 151.6, 151.9, 153.3, 167.4, 169.1, 174.4; MS (ESI): 785 [M$^+$+H].

Example 9

4β-(E)-3-(4-nitrophenyl)-2-(3,4,5-trimethoxyphenyl) acrylamidopodophyllotoxin (3i)

4β-aminopodophyllotoxin (formula 1) (200 mg, 0.48 mmol) was dissolved in 20 ml of dried dichloromethane, followed by addition of aromatic acrylic acid 2i (204 mg, 0.57 mmol) and EDCI (108 mg, 0.57 mmol) and catalytic amount of HOBt. The reaction mixture was stirred at 27° C. for 3 h. Acetic acid (0.4 ml) was added. The reaction mixture was filtered. The filtrate was washed with saturated solution of NaHCO$_3$, 10% hydrochloric acid and water respectively, dried over anhydrous Na$_2$SO$_4$ and chromatographed through silica gel using ethyl acetate/hexane (2:8) as an eluent to obtain the pure product. Yield 98%. Mp: 187-190° C., $[\alpha]_D^{25}$=+7.0 (c=0.5 in CHCl$_3$); $^1$H NMR (400 MHz, CDCl$_3$) δ: 2.56-2.68 (dd, 1H, J=5.1, 5.1 Hz), 2.91-3.10 (m, 1H), 3.73 (s, 6H), 3.75 (s, 6H), 381 (s, 3H), 3.91 (s, 3H), 4.25-4.35 (m, 1H), 4.46-4.57 (m, 2H), 5.35 (t, 1H), 5.82 (d, 1H, J=7.3 Hz), 5.97 (d, 2H, J=5.1 Hz), 6.27 (s, 2H), 6.38 (s, 2H), 6.51 (s, 1H), 6.73 (s, 1H), 7.22 (d, 2H, J=8.8 Hz), 7.86 (s, 1H), 8.07 (d, 2H, J=8.8 Hz); $^{13}$C NMR (75 MHz, CDCl$_3$) δ: 36.6, 43.0, 47.7, 55.6, 59.8, 60.0, 68.5, 101.2, 107.0, 109.0, 109.2, 109.3, 123.1, 129.9, 130.5, 131.7, 132.1, 135.7, 136.2, 137.5, 138.0, 139.9, 142.5, 146.5, 147.1, 147.5, 151.9, 152.9, 167.5, 174.5; MS (ESI): 777 [M$^+$+Na].

Example 10

4β-(E)-3-(3-nitrophenyl)-2-(3,4,5-trimethoxyphenyl) acrylamido podophyllotoxin (3j)

4β-aminopodophyllotoxin (formula 1) (200 mg, 0.48 mmol) was dissolved in 20 ml of dried dichloromethane, followed by addition of aromatic acrylic acid 2j (204 mg, 0.57 mmol) and EDCI (108 mg, 0.57 mmol) and catalytic amount of HOBt. The reaction mixture was stirred at 27° C. for 3 h. Acetic acid (0.4 ml) was added. The reaction mixture was filtered. The filtrate was washed with saturated solution of NaHCO$_3$, 10% hydrochloric acid and water respectively, dried over anhydrous Na$_2$SO$_4$ and chromatographed through silica gel using ethyl acetate/hexane (2:8) as an eluent to obtain the pure product. Yield 98%. Mp: 181-184° C., $[\alpha]_D^{25}$=+8.5 (c=0.5 in CHCl$_3$); $^1$H NMR (400 MHz, CDCl$_3$) δ: 2.54-2.62 (dd, 1H, J=5.0, 5.0 Hz), 2.90-3.03 (m, 1H), 3.73 (s, 6H), 3.74 (s, 6H), 3.77 (s, 3H), 3.88 (s, 3H), 3.89-3.90 (m, 1H), 4.43-4.50 (m, 2H), 5.25-5.30 (m, 1H), 5.82 (d, 1H, J=6.9 Hz), 5.94-5.98 (dd, 2H, J=1.1, 1.1 Hz), 6.22 (s, 2H), 6.38 (s, 2H), 6.45 (s, 1H), 6.73 (s, 1H), 7.40-7.43 (m, 2H), 7.77-7.81 (m, 2H), 8.04-8.09 (m, 1H); MS (ESI): 755 [M$^+$+H].

Example 11

4β-(E)-3-(2-nitrophenyl)-2-(3,4,5-trimethoxyphenyl) acrylamidopodophyllotoxin (3k)

4β-aminopodophyllotoxin (formula 1) (200 mg, 0.48 mmol) was dissolved in 20 ml of dried dichloromethane, followed by addition of aromatic acrylic acid 2k (204 mg, 0.57 mmol) and EDCI (108 mg, 0.57 mmol) and catalytic amount of HOBt. The reaction mixture was stirred at 26° C. for 3 h. Acetic acid (0.4 ml) was added. The reaction mixture was filtered. The filtrate was washed with saturated solution of NaHCO$_3$, 10% hydrochloric acid and water respectively, dried over anhydrous Na$_2$SO$_4$ and chromatographed through silica gel using ethyl acetate/hexane (3:7) as an eluent to obtain the pure product. Yield 97%. Mp: 197-200° C., $[\alpha]_D^{25}$=+1.7 (c=0.5 in CHCl$_3$); $^1$H NMR (400 MHz, CDCl$_3$) δ: 2.61-2.69 (dd, 1H, J=4.5, 4.5 Hz), 2.91-3.04 (m, 1H), 3.60 (s, 6H), 3.74 (s, 6H), 3.76 (s, 3H), 3.77 (s, 3H), 4.05-4.14 (m, 1H), 4.23-4.31 (m, 1H), 4.45-4.54 (m, 2H), 5.35 (t, 1H), 5.88 (d, 1H, J=6.7 Hz), 5.96 (d, 2H, J=8.3 Hz), 6.22 (s, 2H), 6.25 (s, 2H), 6.47 (s, 1H), 6.82 (s, 1H), 6.93 (t, 1H), 7.35-7.40 (m, 2H), 7.93 (s, 1H), 8.03 (t, 1H); $^{13}$C NMR (75 MHz, CDCl$_3$) δ: 36.6, 40.2, 40.3, 43.0, 47.7, 55.4, 55.6, 59.8, 68.5, 101.2, 107.5, 108.0, 109.2, 124.2, 128.8, 129.6, 129.9, 131.3, 131.4, 132.1, 132.2, 133.3, 135.7, 136.2, 137.1, 138.3, 146.5, 147.1, 147.8, 151.9, 167.2, 174.4; MS (ESI): 755 [M$^+$+H].

Example 12

4β-(E)-2-(2-methoxyphenyl)-3-(4-nitrophenyl)acrylamidopodophyllotoxin (3l)

4β-aminopodophyllotoxin (formula 1) (200 mg, 0.48 mmol) was dissolved in 20 ml of dried dichloromethane, followed by addition of aromatic acrylic acid 2l (170 mg, 0.57 mmol) and EDCI (108 mg, 0.57 mmol) and catalytic amount of HOBt. The reaction mixture was stirred at 27° C. for 3 h. Acetic acid (0.4 ml) was added. The reaction mixture was filtered. The filtrate was washed with saturated solution of NaHCO$_3$, 10% hydrochloric acid and water respectively, dried over anhydrous Na$_2$SO$_4$ and chromatographed through silica gel using ethyl acetate/hexane (2:8) as an eluent to obtain the pure product. Yield 98%. Mp: 181-183° C., $[\alpha]_D^{25}$=−4.5 (c=0.5 in CHCl$_3$); $^1$H NMR (400 MHz, CDCl$_3$) δ: 2.43-2.50 (dd, 1H, J=4.7, 4.7 Hz), 2.88-3.01 (m, 1H), 3.74 (s, 6H), 3.77 (s, 3H), 383 (s, 3H), 4.06-4.13 (m, 1H), 4.24-4.30 (dd, 1H, J=3.3, 3.3 Hz), 4.42-4.49 (m, 2H), 5.61 (d, 1H, J=6.7 Hz), 5.95 (s, 2H), 6.20 (s, 2H), 6.42 (s, 1H), 6.69 (s, 1H), 6.92-7.02 (m, 3H), 7.12 (d, 2H, J=8.8 Hz), 7.41 (t, 1H), 7.83 (s, 1H), 8.02 (d, 2H, J=8.8 Hz); $^{13}$C NMR (75 MHz, CDCl$_3$) δ: 36.6, 43.1, 47.1, 55.2, 55.6, 59.8, 64.5, 68.3, 101.1, 108.0, 108.9, 109.3, 111.5, 119.2, 120.7, 123.3, 124.0, 130.3, 131.3, 132.0, 132.1, 135.7, 136.2, 137.9, 139.2, 142.4, 146.2, 146.5, 147.1, 151.9, 157.0, 174.6; MS (ESI): 696 [M$^+$+H].

Example 13

4β-(E)-2-(2-methoxyphenyl)-3-(2-nitrophenyl)acrylamidopodophyllotoxin (3m)

4β-aminopodophyllotoxin (formula 1) (200 mg, 0.48 mmol) was dissolved in 20 ml of dried dichloromethane, followed by addition of aromatic acrylic acid 2m (170 mg, 0.57 mmol) and EDCI (108 mg, 0.57 mmol) and catalytic amount of HOBt. The reaction mixture was stirred at 27° C. for 3 h. Acetic acid (0.4 ml) was added. The reaction mixture was filtered. The filtrate was washed with saturated solution of NaHCO$_3$, 10% hydrochloric acid and water respectively, dried over anhydrous Na$_2$SO$_4$ and chromatographed through silica gel using ethyl acetate/hexane (3:7) as an eluent to obtain the pure product. Yield 98%. Mp: 187-190° C., $[\alpha]_D^{25}$=−59.9 (c=0.5 in CHCl$_3$); $^1$H NMR (400 MHz, CDCl$_3$) δ: 2.47-2.54 (dd, 1H, J=5.2, 2.2 Hz), 2.86-3.00 (m, 1H), 3.73 (s, 6H), 3.73 (s, 6H), 3.76 (s, 3H), 3.83 (s, 3H), 4.02 (t, 1H, J=9.8, 9.8 Hz), 5.94 (d, 2H, J=3.0 Hz), 6.20 (s, 2H), 6.39 (s, 1H), 6.76 (s, 1H), 6.80-6.92 (m, 3H), 7.20-7.33 (m, 5H), 8.03 (s, 1H); $^{13}$C NMR (75 MHz, CDCl$_3$): δ 36.6, 40.5, 43.1, 47.1, 55.2, 55.7, 59.8, 68.3, 101.2, 108.0, 108.9, 109.3, 111.0, 120.3, 124.3, 128.9, 129.8, 130.3, 131.2, 131.5, 131.6, 131.8, 132.0, 133.2, 135.7, 136.2, 136.4, 146.5, 147.1, 147.7, 151.9, 157.2, 167.6, 174.6; MS (ESI): 695 [M$^+$+H].

Example 14

4β-(E)-3-(4-methoxyphenyl)-2-(3,4,5-trimethoxyphenyl)acrylamidopodophyllotoxin (3n)

4β-aminopodophyllotoxin (formula 1) (200 mg, 0.48 mmol) was dissolved in 20 ml of dried dichloromethane, followed by addition of aromatic acrylic acid 2n (196 mg, 0.57 mmol) and EDCI (108 mg, 0.57 mmol) and catalytic amount of HOBt. The reaction mixture was stirred at 27° C. for 3 h. Acetic acid (0.4 ml) was added. The reaction mixture was filtered. The filtrate was washed with saturated solution of NaHCO$_3$, 10% hydrochloric acid and water respectively, dried over anhydrous Na$_2$SO$_4$ and chromatographed through silica gel using ethyl acetate/hexane (3:7) as an eluent to obtain the pure product. Yield 98%. Mp: 128-130° C., $[\alpha]_D^{25}$=−0.49 (c=0.5 in CHCl$_3$); $^1$H NMR (400 MHz, CDCl$_3$) δ: 2.55-2.66 (dd, 1H, J=4.4, 5.1 Hz), 2.87-3.07 (m, 1H), 3.74 (s, 12H), 3.78 (s, 3H), 380 (s, 3H), 3.91 (s, 3H), 4.25-4.34 (m, 1H), 4.45-4.55 (m, 2H), 5.32 (t, 1H), 5.69 (d, 1H, J=6.6 Hz), 5.96 (d, 2H, J=4.4 Hz), 6.26 (s, 2H), 6.43 (s, 2H), 6.48 (s, 1H), 6.69-6.74 (m, 3H), 6.99 (d, 2H, J=8.8 Hz), 7.78 (s, 1H); $^{13}$C NMR (75 MHz, CDCl$_3$) δ: 36.7, 40.2, 40.3, 43.1, 47.7, 55.0, 55.6, 59.7, 59.9, 68.6, 101.1, 104.1, 107.0, 108.0, 109.2, 113.5, 127.2, 130.1, 131.2, 132.0, 133.6, 134.2, 135.7, 136.2, 137.0, 146.5, 147.1, 151.9, 153.0, 159.2, 167.8, 174.5; MS (ESI): 740 [M$^+$+H].

Example 15

4β-(E)-3-(3-methoxyphenyl)-2-(3,4,5-trimethoxyphenyl)acrylamidopodophyllotoxin (3o)

4β-aminopodophyllotoxin (formula 1) (200 mg, 0.48 mmol) was dissolved in 20 ml of dried dichloromethane, followed by addition of aromatic acrylic acid 2o (196 mg, 0.57 mmol) and EDCI (108 mg, 0.57 mmol) and catalytic amount of HOBt. The reaction mixture was stirred at 25° C. for 3 h. Acetic acid (0.4 ml) was added. The reaction mixture was filtered. The filtrate was washed with saturated solution of NaHCO$_3$, 10% hydrochloric acid and water respectively, dried over anhydrous Na$_2$SO$_4$ and chromatographed through silica gel using ethyl acetate/hexane (3:7) as an eluent to obtain the pure product. yield 98%. Mp: 187-190° C., $[\alpha]_D^{25}$=−6.9 (c=0.5 in CHCl$_3$); $^1$H NMR (400 MHz, CDCl$_3$) δ: 2.51-2.58 (dd, 1H, J=4.8, 4.8 Hz), 2.85-3.00 (m, 1H), 3.71 (s, 3H), 3.72 (s, 6H), 3.75 (s, 6H), 3.76 (s, 3H), 3.86 (s, 3H), 4.04-4.10 (m, 1H), 4.24-4.28 (dd, 1H, J=4.0, 4.8 Hz), 4.43-4.46 (m, 2H), 5.66 (d, 1H, J=6.4 Hz), 5.93 (d, 2H, J=8.0 Hz), 6.20 (s, 2H), 6.36-6.44 (m, 4H), 6.66 (d, 1H, J=8.8 Hz), 6.72 (s, 1H), 6.93-7.02 (m, 2H), 7.70 (s, 1H); $^{13}$C NMR (75 MHz, CDCl$_3$) δ: 36.8, 40.4, 43.1, 47.8, 55.0, 55.7, 55.8, 59.8, 60.0, 68.6, 101.2, 106.5, 107.0, 108.0, 109.2, 109.3, 113.5, 113.7, 127.3, 130.1, 131.2, 131.3, 132.0, 132.1, 132.2, 133.7, 134.2, 135.7, 136.2, 137.1, 138.5, 146.5, 147.1, 151.9, 153.1, 159.2, 159.9, 167.9, 174.6; MS (ESI): 740 [M$^+$+H].

Example 16

4β-(E)-3-(4-hydroxyphenyl)-2-(3,4,5-trimethoxyphenyl)acrylamidopodophyllotoxin (3p)

4β-aminopodophyllotoxin (formula 1) (200 mg, 0.48 mmol) was dissolved in 20 ml of dried dichloromethane, followed by addition of aromatic acrylic acid 2p (188 mg, 0.57 mmol) and EDCI (108 mg, 0.57 mmol) and catalytic amount of HOBt. The reaction mixture was stirred at 27° C. for 3 h. Acetic acid (0.4 ml) was added. The reaction mixture was filtered. The filtrate was washed with saturated solution of NaHCO$_3$, 10% hydrochloric acid and water respectively, dried over anhydrous Na$_2$SO$_4$ and chromatographed through silica gel using ethyl acetate/hexane (1:1) as an eluent to obtain the pure product. Yield 98%. Mp: 137-140° C., $[\alpha]_D^{25}$−4.9 (c=0.5 in CHCl$_3$); $^1$H NMR (400 MHz, CDCl$_3$) δ: 2.52-2.64 (dd, 1H, J=5.1, 5.1 Hz), 2.84-3.03 (m, 1H), 3.71 (s, 6H), 3.74 (s, 6H), 3.77 (s, 3H), 3.85 (s, 3H), 4.23-4.32 (m, 1H), 4.40-4.51 (m, 2H), 5.29 (t, 1H), 5.76 (d, 1H, J=6.6 Hz), 5.96 (d, 2H, J=2.9 Hz), 6.22 (s, 2H), 6.38 (s, 2H), 6.44 (s, 1H), 6.75 (s, 1H), 6.91 (d, 2H, J=8.8 Hz), 7.03 (d, 2H, J=8.8 Hz); MS (ESI): 764 [M$^+$+K].

Example 17

Biological Activity

In Vitro Evaluation of Anticancer Activity

Compounds 3a-p have been evaluated for their in vitro cytotoxicity in selected human cancer cell lines i.e., colon (Colo205), lung (Hop-62, A549), oral (KB, DWD, Gurav), Ovarian (A-2780) and breast (MCF7, Zr-75-1) origin by employing the sulforhodamine B (SRB) assay method (Skehn, P.; Storeng, R.; Scudiero, A.; Monks, J.; McMohan, D.; Vistica, D.; Jonathan, T. W.; Bokesch, H.; Kenney, S.; Boyd M. R. J. *Natl. Cancer Inst.* 1990, 82, 1107). The results are summarized with podophyllotoxin and standard drug Adriamycin in Table 1. All the new compounds were significantly cytotoxic towards the colon, breast, lung, oral and ovarian cell lines compared to the standard drug tested, with the concentration of the drug that produced 50% inhibition of cell growth (GI$_{50}$).

Procedure of the SRB-Assay

Single cell suspension of the tumour cells grown in tissue culture were made, cells counted and cell count adjusted to 1×10$^5$ to 5×10$^5$ cells/ml. Ninety six (96) well plates were seeded with this cell suspension, each well receiving 100 μl of it. The plate was then be incubated at 37° C. temperature in CO$_2$ incubator for 24 hours. Drugs were added at concentrations after 24-hour incubation followed by further incubation for 48 hours. Experiment was terminated by gently layering the cells in the wells with 30% TCA and plates were kept in refrigerator for 1 hour following which they were washed thoroughly with tap water, dried attained with 0.4% SRB in 1% acetic aid and finally, the bound SRB eluted with 10 mM tris. Absorbance was read at 540 nm, in the microtitre-plate reader. Optical density of drug-treated cells was compared with that of control cells and cell inhibition was calculated as percent values. Each compound was tested at 10, 20, 40 and 80 μg/ml in triplicate on human malignant cell lines.

TABLE 1

In vitro anticancer activity (GI$_{50}$ μM) data for some representative compounds

| | Breast | | Oral | | | Colon | Lung | | Ovarian |
|---|---|---|---|---|---|---|---|---|---|
| Compound | Zr-75-1 | MCF7 | KB | Gurav | DWD | Colo205 | A-549 | Hop62 | A-2780 |
| 3a | — | — | — | — | — | — | 2.4 | 2.5 | — |
| 3b | — | — | — | — | — | — | 2.9 | 2.9 | — |
| 3c | 2.2 | — | — | 2.4 | — | — | — | 2.5 | — |
| 3d | — | — | — | — | — | — | — | — | — |
| 3e | 2.7 | — | — | 2.5 | — | — | — | — | — |
| 3f | 2.5 | 2.4 | 2.6 | 0.18 | 0.19 | — | 2.1 | 0.17 | 2.7 |
| 3g | 0.18 | 2.7 | 2.2 | 0.19 | <0.1 | 2.0 | — | 0.19 | 2.2 |
| 3h | 2.2 | — | — | 2.6 | 2.9 | 2.7 | — | 2.3 | 2.5 |
| 3i | 2.2 | — | — | 2.1 | 2.4 | 2.1 | — | 2.7 | 2.6 |
| 3j | — | 2.7 | — | 2.1 | <0.1 | — | 2.4 | 0.17 | 2.5 |
| 3k | 2.5 | — | 2.7 | — | — | — | 2.5 | 2.7 | 2.3 |
| 3l | 2.1 | 2.7 | 2.4 | 2.1 | 2.3 | — | <0.1 | 2.0 | 2.3 |
| 3m | 2.2 | 2.8 | 2.5 | 2.2 | 2.3 | — | <0.1 | 2.1 | 2.2 |
| 3n | 2.9 | 2.9 | — | 2.2 | 2.3 | 0.17 | — | — | 2.5 |
| 3o | 0.18 | 2.7 | 2.1 | 2.1 | 2.2 | — | <0.1 | 0.18 | <0.1 |
| 3p | 2.7 | — | 2.6 | 2.7 | 2.7 | — | 2.3 | 2.6 | — |
| ADR | 0.11 | 0.13 | 0.13 | <0.1 | 0.1 | <0.1 | <0.1 | 0.15 | <0.1 |

ADR = adriamycin is the control drug
Etoposide = GI$_{50}$ μM range 0.80-116 (values from NCI database)

In conclusion, the main advantages of the present inventions are that these new 4β-acrylamidopodophyllotoxin congeners of podophyllotoxin have exhibited promising in vitro cytotoxic activity. Further, these compounds have been prepared from podophyllotoxin upon coupling with a variety of substituted-acrylic acids in the presence of EDCI and HOBt at room temperature (25 to 30° C.) provides the new 4β-acrylamidopodophyllotoxin congeners in very good yields.

ADVANTAGES OF THE INVENTION

1. The present invention provides 4β-acrylamidopodophyllotoxin congeners useful as antitumour agents.
2. It also provides a process for the preparation of new 4β-acrylamidopodophyllotoxin congeners useful as antitumour agents.

We claim:
1. A compound of general formula 3

Formula 3 wherein R and R1 are an aryl group and R is selected from 3,4,5-trimethoxyphenyl or 2-methoxy phenyl and R1 is selected from the group consisting of 4-hydroxy-3-methoxyphenyl, 3-hydroxy-4-methoxyphenyl, 4-fluoro-3-methoxyphenyl, 3-fluoro-4-methoxyphenyl, 2-fluoro-5-methoxyphenyl, 2-fluoro-4-methoxyphenyl, 4-hydroxy-3-nitrophenyl, 4-methoxy-3-nitrophenyl, 4-nitrophenyl, 3-nitrophenyl, 2-nitro phenyl, 4-methoxyphenyl, 3-methoxyphenyl and 4-hydroxyphenyl.

2. The compound of claim 1, wherein chemical formulae of the representative compounds are:
4β-(E)-3-(4-hydroxy-3-methoxyphenyl)-2-(3,4,5-trimethoxyphenyl)acrylamidopodophyllotoxin (3a);
4β-(E)-3-(3-hydroxy-4-methoxyphenyl)-2-(3,4,5-trimethoxyphenyl)acrylamidopodophyllotoxin (3b);
4β-(E)-3-(4-fluoro-3-methoxyphenyl)-2-(3,4,5-trimethoxyphenyl)acrylamidopodophyllotoxin (3c);
4β-(E)-3-(3-fluoro-4-methoxyphenyl)-2-(3,4,5-trimethoxyphenyl)acrylamidopodophyllotoxin (3d);
4β-(E)-3-(2-fluoro-5-methoxyphenyl)-2-(3,4,5-trimethoxyphenyl)acrylamidopodophyllotoxin (3e);
4β-(E)-3-(2-fluoro-4-methoxyphenyl)-2-(3,4,5-trimethoxyphenyl)acrylamidopodophyllotoxin (3f);
4β-(E)-3-(4-hydroxy-3-nitrophenyl)-2-(3,4,5-trimethoxyphenyl)acrylamidopodophyllotoxin (3g);
4β-(E)-3-(4-methoxy-3-nitrophenyl)-2-(3,4,5-trimethoxyphenyl)acrylamidopodophyllotoxin (3h);
4β-(E)-3-(4-nitrophenyl)-2-(3,4,5-trimethoxyphenyl) acrylamidopodophyllotoxin (3i);
4β-(E)-3-(3-nitrophenyl)-2-(3,4,5-trimethoxyphenyl) acrylamidopodophyllotoxin (3j);
4β-(E)-3-(2-nitrophenyl)-2-(3,4,5-trimethoxyphenyl) acrylamidopodophyllotoxin (3k);
4β-(E)-2-(2-methoxyphenyl)-3-(4-nitrophenyl)acrylamidopodophyllotoxin (3l);
4β-(E)-2-(2-methoxyphenyl)-3-(2-nitrophenyl)acrylamidopodophyllotoxin (3m);
4β-(E)-3-(4-methoxyphenyl)-2-(3,4,5-trimethoxyphenyl) acrylamidopodophyllotoxin (3n);
4β-(E)-3-(3-methoxyphenyl)-2-(3,4,5-trimethoxyphenyl) acrylamidopodophyllotoxin (3o);
4β-(E)-3-(4-hydroxyphenyl)-2-(3,4,5-trimethoxyphenyl) acrylamidopodophyllotoxin (3p).

3. The compounds as claimed in of claim 1, wherein the structural formula of the representative compounds 3a-p are:

3g

3j

3k

3h

3l

3i

4. A process for the preparation of compound of general formula 3, comprising the steps of:
 (i) dissolving 4β-aminopodophyllotoxin of formula 1 in a solvent to obtain a solution;

(ii) adding aromatic acrylic acid of formula 2a-p in the solution as obtained in step (i) with coupling reagents and acetic acid followed by stirring at temperature in the range of 25 to 30° C. for a period in the range of 2 to 3 h;

(iii) filtering, washing with saturated solution of NaHCO$_3$, 10 hydrochloric acid and followed by water;
(iv) drying the washed filtrate as obtained in step (iii) over anhydrous Na$_2$SO$_4$ followed by chromatography through silica gel using an eluent to obtain the pure product.

5. The process of claim 4, wherein in step (i) the solvent used is selected from the group consisting of dichloromethane, chloroform and tetrahydrofuran.

6. The process of claim 4, wherein in step (ii) the coupling reagents used are N-(3-Dimethylaminopropyl)-N'-ethyl-carbodiimide hydrochloride (EDCI) and 1-HydroxyBenztriazole (HOBt).

7. The process of claim 4, wherein in step (iv) the eluent used is ethyl acetate/hexane in the ratio ranging between 1:1 to 1:4.

8. A method for the treatment of cancer comprising contacting human cancer cells selected from the group consisting of breast, oral, colon, lung and ovarian cancer cells with a compound of general formula 3.

9. The method of claim 8, wherein the compound of general formula 3 exhibits in-vitro anticancer activity against human tumour cells derived from five cancer types selected from the group consisting of breast cancer cell line (MCF-7, Zr-75-1), oral cancer cell line (KB, Gurav, DWD), colon cancer cell line (Colo 205), lung cancer cell line (A549, Hop 62) and ovarion cancer cell line (A-2780).

10. The method of claim 8, wherein concentration of the compound used for in vitro activity against breast cancer cell lines (Zr-75-1) for $GI_{50}$ is in the range of 0.18-2.7 µM at an exposure period of at least 48 hrs.

11. The method of claim 8, wherein concentration of the compound used for in vitro activity against breast cancer cell lines (MCF-7) for $GI_{50}$ is in the range of 2.4-2.9 µM at an exposure period of at least 48 hrs.

12. The method of claim 8, wherein concentration of the compound used for in vitro activity against oral cancer cell lines (KB) for $GI_{50}$ is in the range of 2.1-2.7 µM at an exposure period of at least 48 hrs.

13. The method of claim 8, wherein concentration of the compound used for in vitro activity against oral cancer cell lines (Gurav) for $GI_{50}$ is in the range of 0.18-2.7 µM at an exposure period of at least 48 hrs.

14. The method of claim 8, wherein concentration of the compound used for in vitro activity against oral cancer cell lines (DWD) for $GI_{50}$ is in the range of <0.1-2.9 µM at an exposure period of at least 48 hrs.

15. The method of claim 8, wherein concentration of the compound used for in vitro activity against colon cancer cell lines (Colo205) for $GI_{50}$ is in the range of 0.17-2.7 µM at an exposure period of at least 48 hrs.

16. The method of claim 8, wherein concentration of the compound used for in vitro activity against lung cancer cell lines (A-549) for $GI_{50}$ is in the range of <0.1-2.9 µM at an exposure period of at least 48 hrs.

17. The method of claim 8, concentration of the compound used for in vitro activity against lung cancer cell lines (Hop62) for $GI_{50}$ is in the range of 0.17-2.9 µM at an exposure period of at least 48 hrs.

18. The method of claim 8, wherein concentration of the compound used for in vitro activity against ovarian cancer cell lines (A-2780) for $GI_{50}$ is in the range of <0.1-2.7 µM at an exposure period of at least 48 hrs.

* * * * *